(12) United States Patent
Bangera et al.

(10) Patent No.: US 9,024,814 B2
(45) Date of Patent: May 5, 2015

(54) TRACKING IDENTITIES OF PERSONS USING MICRO-IMPULSE RADAR

(75) Inventors: Mahalaxmi Gita Bangera, Renton, WA (US); Roderick A. Hyde, Redmond, WA (US); Muriel Y. Ishikawa, Livermore, CA (US); Edward K. Y. Jung, Bellevue, WA (US); Jordin T. Kare, Seattle, WA (US); Eric C. Leuthardt, St. Louis, MO (US); Nathan P. Myhrvold, Bellevue, WA (US); Elizabeth A. Sweeney, Seattle, WA (US); Clarence T. Tegreene, Bellevue, WA (US); David B. Tuckerman, Lafayette, CA (US); Thomas A. Weaver, San Mateo, CA (US); Lowell L. Wood, Jr., Bellevue, WA (US); Victoria Y. H. Wood, Livermore, CA (US)

(73) Assignee: The Invention Science Fund I, LLC, Bellevue, WA (US)

( * ) Notice: Subject to any disclaimer, the term of this patent is extended or adjusted under 35 U.S.C. 154(b) by 653 days.

(21) Appl. No.: 12/928,703

(22) Filed: Dec. 16, 2010

(65) Prior Publication Data
US 2011/0285579 A1 Nov. 24, 2011

Related U.S. Application Data

(63) Continuation-in-part of application No. 12/925,407, filed on Oct. 20, 2010, which is a continuation-in-part of application No. 12/924,036, filed on Sep. 17, 2010, which is a continuation-in-part of application No. 12/655,808, filed on Jan. 5, 2010.

(51) Int. Cl.
*G01S 13/08* (2006.01)
*G06Q 30/02* (2012.01)
(Continued)

(52) U.S. Cl.
CPC .............. *G06Q 30/02* (2013.01); *A61B 5/7253* (2013.01); *A61B 5/0816* (2013.01); *G01S 13/88* (2013.01);
(Continued)

(58) Field of Classification Search
CPC .... A61B 5/024; A61B 5/0507; A61B 5/0816; A61B 5/165; A61B 5/7253; G01S 13/52; G01S 13/88; G01S 7/412; G01S 7/415
USPC .............. 342/189, 175, 90; 340/573.1, 573.4, 340/573.7
See application file for complete search history.

(56) References Cited

U.S. PATENT DOCUMENTS

| 3,796,208 A | 3/1974 | Bloice |
| 4,513,748 A | 4/1985 | Nowogrodzki et al. |

(Continued)

FOREIGN PATENT DOCUMENTS

WO   WO 2007/010460 A2   1/2007

OTHER PUBLICATIONS

Azevedo et al.; "Micropower Impulse Radar"; Science and Technology Review; Jan./Feb. 1996; Retrieved from the internet on Feb. 10, 2012 (as provided by Officer); pp. 16-29; located at: https://www.llnl.gov/str/pdfs/01_96.2.pdf.

(Continued)

*Primary Examiner* — Timothy A Brainard
(74) *Attorney, Agent, or Firm* — Dorsey & Whitney LLP

(57) ABSTRACT

One or more human attributes extracted from a micro-impulse radar (MIR) signal is correlated to a temporary identity or phenotypic identity of a person.

43 Claims, 6 Drawing Sheets

(51) Int. Cl.
*A61B 5/00* (2006.01)
*A61B 5/08* (2006.01)
*A61B 5/05* (2006.01)
*A61B 5/16* (2006.01)
*G01S 13/88* (2006.01)
*G01S 7/41* (2006.01)
*G01S 13/52* (2006.01)

(52) U.S. Cl.
CPC ............... *G01S 7/415* (2013.01); *G01S 13/52* (2013.01); *A61B 5/0507* (2013.01); *G01S 7/412* (2013.01); *A61B 5/165* (2013.01)

(56) References Cited

U.S. PATENT DOCUMENTS

| | | | |
|---|---|---|---|
| 4,958,638 | A | 9/1990 | Sharpe et al. |
| 5,226,425 | A | 7/1993 | Righter |
| 5,305,748 | A | 4/1994 | Wilk |
| 5,361,070 | A | 11/1994 | McEwan |
| 5,448,501 | A | 9/1995 | Hablov et al. |
| 5,507,291 | A | 4/1996 | Stirbl et al. |
| 5,519,400 | A | 5/1996 | McEwan |
| 5,573,012 | A | 11/1996 | McEwan |
| 5,766,208 | A | 6/1998 | McEwan |
| 5,774,091 | A | 6/1998 | McEwan |
| 5,850,470 | A * | 12/1998 | Kung et al. ............... 382/157 |
| 5,905,436 | A | 5/1999 | Dwight et al. |
| 6,011,477 | A | 1/2000 | Teodorescu et al. |
| 6,062,216 | A | 5/2000 | Corn |
| 6,083,172 | A | 7/2000 | Baker, Jr. et al. |
| 6,122,537 | A | 9/2000 | Schmidt |
| 6,211,863 | B1 | 4/2001 | Chery et al. |
| 6,218,979 | B1 | 4/2001 | Barnes et al. |
| 6,289,238 | B1 | 9/2001 | Besson et al. |
| 6,292,688 | B1 | 9/2001 | Patton |
| 6,315,719 | B1 | 11/2001 | Rode et al. |
| 6,351,246 | B1 | 2/2002 | McCorkle |
| 6,454,708 | B1 | 9/2002 | Ferguson et al. |
| 6,466,125 | B1 | 10/2002 | Richards et al. |
| 6,489,893 | B1 | 12/2002 | Richards et al. |
| 6,492,906 | B1 | 12/2002 | Richards et al. |
| 6,524,239 | B1 | 2/2003 | Reed et al. |
| 6,608,910 | B1 | 8/2003 | Srinivasa et al. |
| 6,611,206 | B2 | 8/2003 | Eshelman et al. |
| 6,611,783 | B2 | 8/2003 | Kelly, Jr. et al. |
| 6,656,116 | B2 | 12/2003 | Kim et al. |
| 6,661,345 | B1 | 12/2003 | Bevan et al. |
| 6,696,957 | B2 | 2/2004 | Shepher |
| 6,730,023 | B1 * | 5/2004 | Dodds ............... 600/300 |
| 6,753,780 | B2 | 6/2004 | Li |
| 6,950,022 | B2 | 9/2005 | Breed |
| 6,954,145 | B2 | 10/2005 | Nakamura et al. |
| 7,001,334 | B2 | 2/2006 | Reed et al. |
| 7,106,885 | B2 | 9/2006 | Osterweil et al. |
| 7,196,629 | B2 | 3/2007 | Ruoss et al. |
| 7,272,431 | B2 | 9/2007 | McGrath |
| 7,417,581 | B2 | 8/2008 | Fullerton et al. |
| 7,525,434 | B2 * | 4/2009 | Batra ............... 340/572.1 |
| 7,567,200 | B1 * | 7/2009 | Osterweil ............... 342/28 |
| 7,692,573 | B1 | 4/2010 | Funk |
| 7,916,066 | B1 | 3/2011 | Osterweil |
| 8,068,051 | B1 | 11/2011 | Osterweil |
| 8,094,009 | B2 | 1/2012 | Allen et al. |
| 8,125,331 | B2 | 2/2012 | Allen et al. |
| 8,130,095 | B2 | 3/2012 | Allen et al. |
| 8,204,786 | B2 | 6/2012 | LeBoeuf et al. |
| 8,284,046 | B2 | 10/2012 | Allen et al. |
| 8,284,990 | B2 | 10/2012 | Ma et al. |
| 8,311,616 | B2 | 11/2012 | Feldman et al. |
| 8,577,446 | B2 | 11/2013 | Kyle et al. |
| 2003/0033449 | A1 | 2/2003 | Frantz et al. |
| 2003/0058372 | A1 | 3/2003 | Williams et al. |
| 2003/0135097 | A1 | 7/2003 | Wiederhold et al. |
| 2004/0027270 | A1 | 2/2004 | Fullerton et al. |
| 2004/0249257 | A1 | 12/2004 | Tupin, Jr. et al. |
| 2004/0249258 | A1 | 12/2004 | Tupin, Jr. et al. |
| 2005/0015286 | A1 | 1/2005 | Rudnik et al. |
| 2005/0040230 | A1 | 2/2005 | Swartz et al. |
| 2005/0046584 | A1 | 3/2005 | Breed |
| 2005/0163302 | A1 | 7/2005 | Mock et al. |
| 2006/0001545 | A1 | 1/2006 | Wolf |
| 2006/0061504 | A1 | 3/2006 | Leach, Jr. et al. |
| 2006/0218244 | A1 | 9/2006 | Rasmussen et al. |
| 2006/0224051 | A1 | 10/2006 | Teller et al. |
| 2006/0239471 | A1 | 10/2006 | Mao et al. |
| 2007/0121097 | A1 | 5/2007 | Boillot |
| 2007/0136774 | A1 | 6/2007 | Lourie et al. |
| 2007/0149282 | A1 | 6/2007 | Lu et al. |
| 2007/0214371 | A1 | 9/2007 | You et al. |
| 2008/0007445 | A1 | 1/2008 | Leach, Jr. et al. |
| 2008/0021401 | A1 | 1/2008 | Jacobsen et al. |
| 2008/0028206 | A1 | 1/2008 | Sicard et al. |
| 2008/0065468 | A1 | 3/2008 | Berg et al. |
| 2008/0077015 | A1 | 3/2008 | Boric-Lubecke et al. |
| 2008/0098448 | A1 | 4/2008 | Mondesir et al. |
| 2008/0101329 | A1 | 5/2008 | Richards et al. |
| 2008/0146892 | A1 | 6/2008 | LeBoeuf et al. |
| 2008/0165046 | A1 | 7/2008 | Fullerton et al. |
| 2008/0167535 | A1 | 7/2008 | Stivoric et al. |
| 2008/0183090 | A1 | 7/2008 | Farringdon et al. |
| 2008/0240379 | A1 | 10/2008 | Maislos et al. |
| 2008/0270172 | A1 | 10/2008 | Luff et al. |
| 2008/0270238 | A1 | 10/2008 | Zweben et al. |
| 2009/0017910 | A1 | 1/2009 | Rofougaran et al. |
| 2009/0025024 | A1 | 1/2009 | Beser et al. |
| 2009/0052859 | A1 | 2/2009 | Greenberger et al. |
| 2009/0138805 | A1 * | 5/2009 | Hildreth ............... 715/745 |
| 2009/0140851 | A1 | 6/2009 | Graves et al. |
| 2009/0164287 | A1 | 6/2009 | Kies et al. |
| 2009/0284378 | A1 | 11/2009 | Ferren et al. |
| 2009/0296997 | A1 | 12/2009 | Rocheford |
| 2009/0328089 | A1 | 12/2009 | Pradeep et al. |
| 2010/0106475 | A1 | 4/2010 | Smith et al. |
| 2010/0117837 | A1 | 5/2010 | Stirling et al. |
| 2010/0234714 | A1 | 9/2010 | Mercier et al. |
| 2010/0234720 | A1 | 9/2010 | Tupin, Jr. et al. |
| 2010/0241313 | A1 * | 9/2010 | Fiske et al. ............... 701/36 |
| 2010/0259395 | A1 | 10/2010 | Nuthi |
| 2010/0306388 | A1 * | 12/2010 | Newville ............... 709/227 |
| 2011/0080529 | A1 | 4/2011 | Wong |
| 2011/0109545 | A1 | 5/2011 | Touma et al. |
| 2011/0161136 | A1 | 6/2011 | Faith et al. |
| 2011/0307210 | A1 | 12/2011 | Stevens et al. |
| 2012/0116186 | A1 | 5/2012 | Shrivastav et al. |
| 2012/0286955 | A1 | 11/2012 | Welch et al. |
| 2012/0326873 | A1 | 12/2012 | Utter, II |

OTHER PUBLICATIONS

PCT International Search Report; International App. No. PCT US2011/001985; May 2, 2012; pp. 1-5.
Tivive et al.; "A Human Gait Classification Method Based on Radar Doppler Spectrograms"; EURASIP Journal on Advances in Signal Processing; Bearing a date of Feb. 1, 2010; pp. 1-12; vol. 2010; Hindawi Publishing Corporation.
Warren et al.; "Designing Smart Health Care Technology into the Home of the Future"; Sandia National Laboratories; Mar. 25, 1999; pp. 1-18.
Zhang, Zhaonian; "A Micro-Doppler Sonar for Acoustic Surveillance in Sensor Networks"; ProQuest Dissertations and Theses: The Science and Engineering Collection; bearing a date of Aug. 2008; 224 pgs.; ProQuest, LLC.
Michahelles et al.; "Less Contact: Heart-rate detection without even touching the user"; Proceedings of the Eighth International Symposium on Wearable Computers; 2004; vol. 1; pp. 1-4; Retreived from URL: http://ieeexplore.ieee.org/stamp/stamp.jsp?tp=&arnumber=1364682&isnumber=29895 printed on Dec. 26, 2011;IEEE.
PCT International Search Report; International App. No. PCT/ US 11/01629; Jan. 9, 2012; pp. 1-3.
PCT International Search Report; International App. No. PCT/ US2011/001790; Feb. 3, 2012; pp. 1-2.
PCT International Search Report; International App. No. PCT/US 11/01789; Feb. 14, 2012; pp. 1-2.

(56) References Cited

OTHER PUBLICATIONS

PCT International Search Report; International App. No. PCT/US11/00018; Mar. 4, 2011; pp. 1-2.

PCT International Search Report; International App. No. PCT/US 11/00019; Mar. 14, 2011; pp. 1-2.

European Patent Office, Supplementary European Search Report, Pursuant to Rule 62 EPC; App. No. 11834761.6; Apr. 7, 2014; pp. 1-6.

Extended European Search Report; European App. No. EP 11 73 2004; Oct. 7, 2014; pp. 1-6.

\* cited by examiner

US 9,024,814 B2

TRACKING IDENTITIES OF PERSONS USING MICRO-IMPULSE RADAR

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)).

Related Applications

For purposes of the USPTO extra-statutory requirements, the present application constitutes a continuation-in-part of the following United States patent applications:
Application No. 12/925,407, entitled MEDIA OUTPUT WITH MICRO-IMPULSE RADAR FEEDBACK OF PHYSIOLOGICAL RESPONSE, naming Mahalaxmi Gita Bangera, Roderick A. Hyde, Muriel Y. Ishikawa, Edward K. Y. Jung, Jordin T. Kare, Eric C. Leuthardt, Nathan P. Myhrvold, Elizabeth A. Sweeney, Clarence T. Tegreene, David B. Tuckerman, Lowell L. Wood, Jr., and Victoria Y. H. Wood as inventors, filed on Oct. 20, 2010, which is currently co-pending, or is an application of which a currently co-pending application is entitled to the benefit of the filing date;
Application No. 12/924,036 entitled CONTROL OF AN ELECTRONIC APPARATUS USING MICRO-IMPULSE RADAR, naming Mahalaxmi Gita Bangera, Roderick A. Hyde, Muriel Y. Ishikawa, Edward K. Y. Jung, Jordin T. Kare, Eric C. Leuthardt, Nathan P. Myhrvold, Elizabeth A. Sweeney, Clarence T. Tegreene, David B. Tuckerman, Lowell L. Wood, Jr., and Victoria Y. H. Wood as inventors, filed on Sep. 17, 2010, which is currently co-pending, or is an application of which a currently co-pending application is entitled to the benefit of the filing date; and
Application No. 12/655,808, entitled MICRO-IMPULSE RADAR DETECTION OF A HUMAN DEMOGRAPHIC AND DELIVERY OF TARGETED MEDIA CONTENT, naming Mahalaxmi Gita Bangera, Roderick A. Hyde, Muriel Y. Ishikawa, Edward K. Y. Jung, Jordin T. Kare, Eric C. Leuthardt, Nathan P. Myhrvold, Elizabeth A. Sweeney, Clarence T. Tegreene, David B. Tuckerman, Lowell L. Wood, Jr., and Victoria Y. H. Wood as inventors, filed on Jan. 5, 2010, which is currently co-pending, or is an application of which a currently co-pending application is entitled to the benefit of the filing date.

The United States Patent Office (USPTO) has published a notice to the effect that the USPTO's computer programs require that patent applicants reference both a serial number and indicate whether an application is a continuation or continuation-in-part. Stephen G. Kunin, Benefit of Prior-Filed Application, USPTO Official Gazette Mar. 18, 2003, available at http://www.uspto.gov/web/offices/com/sol/og/2003/week11/patbene.htm. The present Applicant Entity (hereinafter "Applicant") has provided above a specific reference to the application(s)from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant is designating the present application as a continuation-in-part of its parent applications as set forth above, but expressly points out that such designations are not to be construed in any way as any type of commentary and/or admission as to whether or not the present application contains any new matter in addition to the matter of its parent application(s). All subject matter of the Related Applications and of any and all parent, grandparent, great-grandparent, etc. applications of the Related Applications is incorporated herein by reference to the extent such subject matter is not inconsistent herewith.

SUMMARY

According to an embodiment, a method for correlating a temporary identity to at least one person includes receiving a micro-impulse radar (MIR) signal including information associated with at least one person; performing analysis of the micro-impulse radar signal to determine, from the signal, one or more attributes of the at least one person, including at least one physical attribute and/or at least one physiological attribute; and correlating a temporary identity to one or more of the at least one person based at least in part on the attribute(s). The attributes can include a plurality of attributes including at least one physical attribute and at least one physiological attribute.

According to an embodiment, a non-transient computer-readable medium carries computer-readable instructions configured to cause a computer to perform steps including receiving a MIR signal including information associated with at least one person; performing analysis of the MIR signal to determine, from the signal, one or more attributes of the at least one person; and correlating a temporary identity to the at least one person based at least in part on the one or more attributes.

According to an embodiment, a system for providing a probabilistic identification of a person includes a MIR configured to capture signals; a signal processor configured to receive the signals from the MIR and extract from the signals information corresponding to one or more attributes corresponding to a human form; a controller configured to receive the attribute(s) and determine a phenotypic identity corresponding to the attribute(s); and an electronic memory and/or a computer storage device configured to receive and hold the information corresponding to the attribute(s) and the assigned phenotypic identity. The attribute(s) can include at least one physical attribute and at least one physiological attribute.

According to an embodiment, a method for identifying an individual from a group of individuals includes accessing an identification library including a plurality of individual identities and their phenotypic identities; receiving at least one MIR signal including information associated with at least one human form; performing analysis on the MIR signal to extract a phenotypic profile corresponding to the at least one human form; and comparing the phenotypic profile to the plurality of phenotypic identities from the identification library to determine an associated individual identity.

According to an embodiment, non-transient computer-readable medium carries computer-readable instructions configured to cause a computer to perform steps including accessing an identification library including a plurality of individual identities and their phenotypic identities; receiving at least one MIR signal including information associated with at least one human form; performing analysis on the MIR signal to extract a phenotypic profile corresponding to the at least one human form; and comparing the phenotypic profile to the plurality of phenotypic identities from the identification library to determine an associated individual identity.

According to an embodiment, a method for determining an individual identity from MIR data includes receiving a phenotypic identity including one or more human attributes extracted from MIR data and correlating the phenotypic identity to an individual identity.

According to an embodiment, a method for determining individual preferences from a phenotypic identity includes receiving a phenotypic identity including one or more human attributes extracted from MIR data and correlating the phenotypic identity to individual preferences.

According to an embodiment, a non-transient computer-readable medium carries computer-readable data including at least one phenotypic identity corresponding to at least one person and one or more preferences of the at least one person corresponding to one or more parameters for operating one or more apparatuses.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

Figure 1:
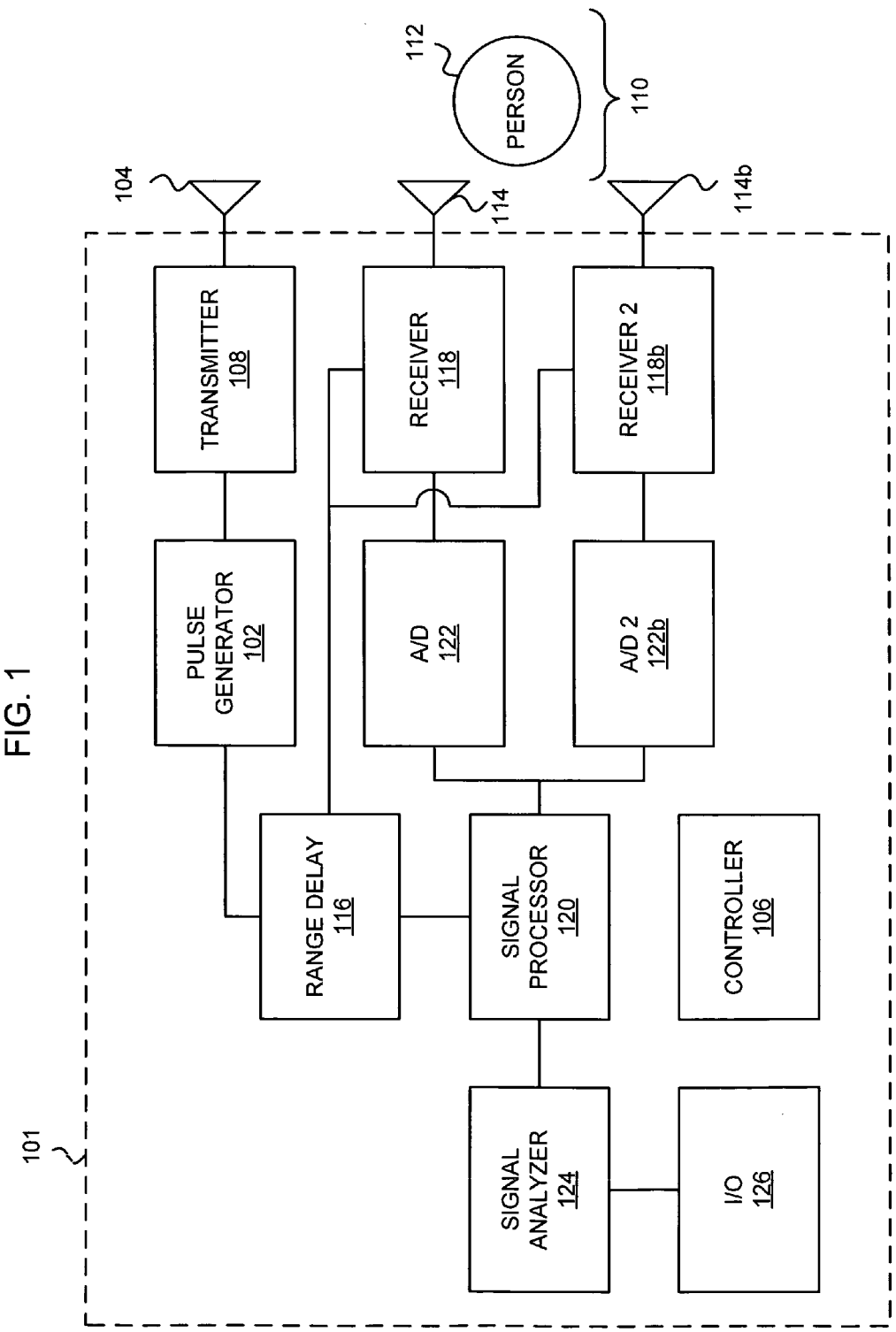
FIG. 1 is a simplified block diagram of a micro-impulse radar (MIR), according to an embodiment.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments can be utilized, and other changes can be made, without departing from the spirit or scope of the subject matter presented here.

FIG. 1 is a simplified block diagram of a micro-impulse radar (MIR) 101, according to an embodiment. A pulse generator 102 is configured to output a relatively short voltage pulse that is applied to a transmit antenna 104. A typical transmitted pulse width can be between about two hundred picoseconds and about 5 nanoseconds, for example. The voltage pulse can be conditioned and amplified (or attenuated) for output by a transmitter 108. For example, the transmitter 108 can transmit the voltage pulse or can further condition the pulse, such as by differentiating a leading and/or trailing edge to produce a short sub-nanosecond transmitted pulses. The voltage pulse is typically not modulated onto a carrier frequency. Rather, the voltage pulse transmission spectrum is the frequency domain transform of the emitted pulse. The MIR 101 can probe a region 110 by emitting a series of spaced voltage pulses. For example, the series of voltage pulses can be spaced between about 100 nanoseconds and 100 microseconds apart. Typically, the pulse generator 102 emits the voltage pulses with non-uniform spacing such as random or pseudo-random spacing, although constant spacing can be used if interference or compliance is not a concern. Spacing between the series of voltage pulses can be varied responsive to detection of one or more persons 112 in the region 110. For example, the spacing between pulses can be relatively large when a person 112 is not detected in the region 110. Spacing between pulses can be decreased (responsive to one or more commands from a controller 106) when a person 112 is detected in the region 110. For example, the decreased time between pulses can result in faster MIR data generation for purposes of more quickly determining information about one or more persons 112 in the region 110. The emitted series of voltage pulses can be characterized by spectral components having high penetration that can pass through a range of materials and geometries in the region 110.

An object 112 (such as a person) in the probed region 110 can selectively reflect, refract, absorb, and/or otherwise scatter the emitted pulses. A return signal including a reflected, refracted, absorbed, and/or otherwise scattered signal can be received by a receive antenna 114. Optionally, the receive antenna 114 and transmit antenna 104 can be combined into a single antenna. In a single antenna embodiment, a filter (not shown) can be used to separate the return signal from the emitted pulse.

A probed region 110 can be defined according to an angular extent and distance from the transmit antenna 104 and the receive antenna 114. Distance can be determined by a range delay 116 configured to trigger a receiver 118 operatively coupled to the receive antenna 114. For example, the receiver 118 can include a voltage detector such as a capture-and-hold capacitor or network. The range delay corresponds to distance into the region 110. Range delay can be modulated to capture information corresponding to different distances.

A signal processor 120 can be configured to receive detection signals or data from the receiver 118 and the analog to digital converter 122, and by correlating range delay to the detection signal, extract data corresponding to the probed region 110 including the object 112.

Optionally, the MIR 101 can include a second receive antenna 114b. The second receive antenna can be operatively coupled to a second receiver 118b coupled to an output of the range delay 116 or a separate range delay (not shown) configured to provide a delay selected for a depth into the region 110. The signal processor 120 can further receive output from a second A/D converter 122b operatively coupled to the second receiver 118b.

The signal processor 120 can be configured to compare detection signals received by the antennas 114, 114b. For example, the signal processor 120 can search for common signal characteristics such as similar reflected static signal strength or spectrum, similar (or corresponding) Doppler shift, and/or common periodic motion components, and compare the respective range delays corresponding to detection by the respective antennas 114, 114b. Signals sharing one or more characteristics can be correlated to triangulate to a location of one or more objects 112 in the region 110 relative to known locations of the antennas 114, 114b. The triangulated locations can be output as computed ranges of angle or computed ranges of extent.

For example, a first signal corresponding to a reflected pulse received by an antenna element 114 can be digitized by an analog-to-digital converter (A/D) 122 to form a first digitized waveform. A second signal corresponding to the reflected pulse received by a second antenna element 114b can similarly be digitized by and A/D 122b (or alternatively by the same A/D converter 122) to form a second digitized waveform. The signal processor 120 can compare the first and second digitized waveforms and deduce angular information from the first and second digitized waveforms and known geometry of the first and second antenna elements.

A second pulse can be received at a second range delay 116 value and can be similarly signal processed to produce a second set of angular information that maps a second surface at a different distance. Depth within a given range delay can be inferred from a strength of the reflected signal. A greater number of signals can be combined to provide additional depth information. A series of pulses can be combined to form a time series of signals corresponding to the object 112 that includes movement information of the object 112 through the region 110. The object 112 described herein can include one or more persons.

The signal processor 120 outputs MIR data. The MIR data can include object location information, object shape information, object velocity information, information about inclusion of high density and/or conductive objects such as jewelry, cell phones, glasses including metal, etc., and physiological information related to periodic motion. The MIR data can include spatial information, time-domain motion information, and/or frequency domain information. Optionally, the MIR data can be output in the form of an image. MIR data in the form of an image can include a surface slice made of pixels or a volume made of voxels. Optionally, the image can include vector information.

The MIR data from the signal processor 120 is output to a signal analyzer 124. The signal analyzer 124 can be integrated with the signal processor 120 and/or can be included in the same MIR 101, as shown. Alternatively, the signal processor 120 can output MIR data through an interface to a signal analyzer 124 included in an apparatus separate from the MIR 101.

A signal analyzer 124 can be configured to extract desired information from MIR data received from the signal processor 120. Data corresponding to the extracted information can be saved in a memory for access by a data interface 126 or can be pushed out the data interface 126.

The signal analyzer 124 can be configured to determine the presence of a person 112 in the region 110. For example, MIR data from the signal processor can include data having a static spectrum at a location in the region 110, and a periodic motion spectrum corresponding to the location characteristic of a human physiological process (e.g. heartbeat and/or breathing). From the correspondence of such MIR data, it can be deduced that a person 112 is at the location in the region 110. The signal analyzer 124 can be configured to determine a number of persons 112 in the region 110. The signal analyzer 124 can be configured to determine the size of a person and/or relative size of anatomical features of a person 112 in the region 110. The signal analyzer 124 can be configured to determine the presence of an animal 112 in the region 110. The signal analyzer 124 can be configured to determine movement and/or speed of movement of a person 112 through the region 110. The signal analyzer 124 can be configured to determine or infer the orientation of a person 112 such as the direction a person is facing relative to the region 110. The signal analyzer 124 can be configured to determine one or more physiological aspects of a person 112 in the region 110. The signal analyzer 124 can determine presence of a personal appliance such as a cell phone, PDA, etc. and/or presence of metalized objects such as credit cards, smart cards, access cards, etc. The signal analyzer 124 can infer the gender and age of one or more persons based on returned MIR data. For example, male bodies can generally be characterized by higher mass density than female bodies, and thus can be characterized by somewhat greater reflectivity at a given range. Adult female bodies can exhibit relatively greater harmonic motion ("jiggle") responsive to movements, and can thus be correlated to harmonic spectra characteristics. Older persons generally move differently than younger persons, allowing an age inference based on detected movement in the region 110.

By determination of one or more such aspects and/or combinations of aspects, the signal analyzer 124 can determine a demographic of one or more persons 112 in the region 110.

For example, MIR data can include movement corresponding to the beating heart of one or more persons 112 in the region 110. The signal analyzer 124 can filter the MIR data to remove information not corresponding to a range of heart rates, and determine one or more heart rates by comparing movement of the heart surface to the MIR signal rate. The one or more heart rates can further be characterized according to a confidence factor, depending on statistical certainty regarding the determined one or more heart rates.

Similarly, the signal analyzer 124 can determine one or more respiration rates by measuring movement corresponding to the chest or diaphragm of one or more persons 112. The signal analyzer 124 can determine movement, a direction of movement, and/or a rate of movement of one or more persons 112 in the region 110. Operation of the signal analyzer 124 is described in greater detail below by reference to FIGS. 2 and 3.

An electronic controller 106 can be operatively coupled to the pulse generator 102, the transmitter 108, the range delay 116, the receiver 118, the analog-to-digital converter 122, the signal processor 120, and/or the signal analyzer 124 to control the operation of the components of the MIR 101. For embodiments so equipped, the electronic controller 106 can also be operatively coupled to the second receiver 118b, and the second analog-to-digital converter 122b. The data interface 126 can include a high speed interface configured to output data from the signal analyzer 124. Alternatively, for cases where signals are analyzed externally to the MIR, the data interface 126 can include a high speed interface configured to output MIR data from the signal processor 120. The data interface 126 can include an interface to the controller 106. Optionally, the controller 106 can be interfaced to external systems via a separate interface (not shown).

Figure 2:
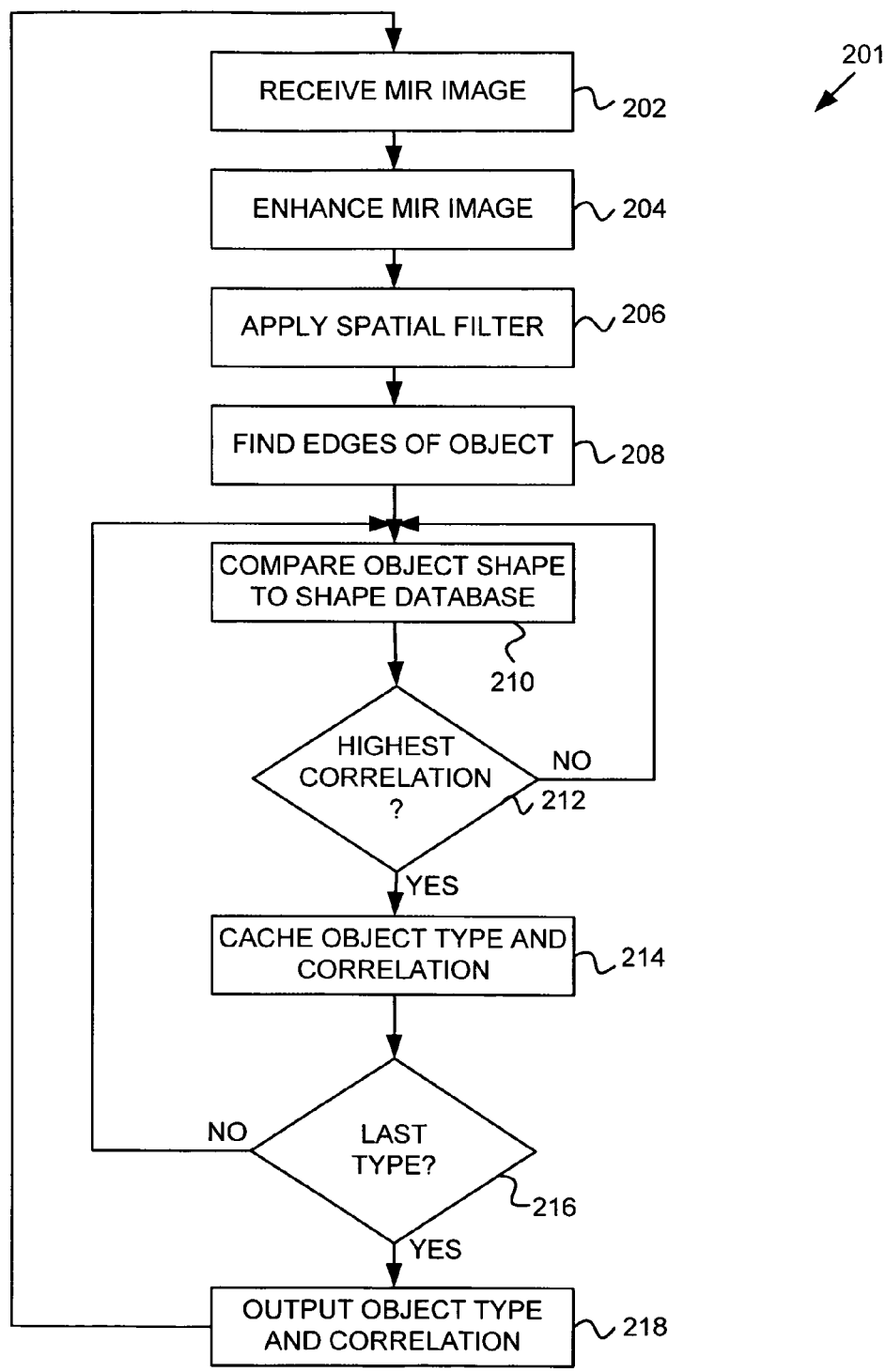
FIG. 2 is a flow chart showing an illustrative process for determining the presence of a person in a region with the MIR of FIG. 1, according to an embodiment.

FIG. 2 is a flow chart showing an illustrative process 201 for determining the presence of one or more persons 112 in the region 110 with the signal analyzer 124 of the MIR 101, according to an embodiment. Beginning with step 202, MIR data is received as described above in conjunction with FIG. 1. The MIR data can correspond to a plurality of probes of the region 110. Proceeding to optional step 204, the MIR data can be enhanced to facilitate processing. For example, grayscale data corresponding to static reflection strength as a function of triangulated position can be adjusted, compressed, quantized, and/or expanded to meet a desired average signal brightness and range. Additionally or alternatively, velocity information corresponding to Doppler shift, and/or frequency transform information corresponding to periodically varying velocity can similarly be adjusted, compressed, quantized, and/or expanded. Systematic, large scale variations in brightness can be balanced, such as to account for side-to-side variations in antenna coupling to the region. Contrast can be enhanced such as to amplify reflectance variations in the region.

Proceeding to optional step 206, a spatial filter can be applied. Application of a spatial filter can reduce processing time and/or capacity requirements for subsequent steps described below. The spatial filter may, for example, include a computed angle or computed extent filter configured to remove information corresponding to areas of contrast, velocity, or frequency component(s) having insufficient physical extent to be large enough to be an object of interest. The spatial filter may, for example, identify portions of the region 110 having sufficient physical extent to correspond to body parts or an entire body of a person 112, and remove features corresponding to smaller objects such as small animals, leaves of plants, or other clutter. According to an embodiment, the spatial filter can remove information corresponding to areas of contrast, velocity, or frequency component(s) having physical extent greater than a maximum angle or extent that is likely to correspond to a person or persons 112. In other embodiments, the spatial filter applied in step 206 can eliminate small, low contrast features, but retain small, high contrast features such as jewelry, since such body ornamentation can be useful in some subsequent processes. The step of applying the spatial filter 206 can further include removing background features from the MIR data. For example, a wall lying between an antenna 104, 114 and the region 110 can cast a shadow such as a line in every MIR signal. Removal of such constant features can reduce subsequent processing requirements.

Proceeding to optional step 208, an edge-finder can identify edges of objects 112 in the region 110. For example, a global threshold, local threshold, second derivative, or other algorithm can identify edge candidates. Object edges can be used, for example, to identify object shapes, and thus relieve subsequent processes from operating on grayscale data. Alternatively, step 208 can be omitted and the process of identifying objects can be performed on the grayscale MIR data.

Proceeding to step 210, processed data corresponding to the MIR data is compared to a database to determine a match. The object data received from step 202 (and optionally steps 204, 206, and/or 208) can be compared to corresponding data for known objects in a shape database. Step 210 can be performed on a grayscale signal, but for simplicity of description it will be assumed that optional step 208 was performed and matching is performed using object edges, velocity, and/or spectrum values. For example, the edge of an object 112 in the region 110 can include a line corresponding to the outline of the head and torso, cardiac spectrum, and movements characteristic of a young adult male. A first shape in the shape database can include the outline of the head and torso, cardiac spectrum, density, and movements characteristic of a young adult female and/or the head and torso outline, cardiac spectrum, density, and movements characteristic of a generic human. The differences between the MIR data and the shape database shape can be measured and characterized to derive a probability value. For example, a least-squares difference can be calculated.

Optionally, the object shape from the MIR data can be stepped across, magnified, and stepped up and down the shape database data to minimize a sum-of-squares difference between the MIR shape and the first shape in the shape database. The minimum difference corresponds to the probability value for the first shape.

Proceeding to step 212, if the probability value for the first shape is the best probability yet encountered, the process proceeds to step 214. For the first shape tested, the first probability value is the best probability yet encountered. If an earlier tested shape had a higher probability to the MIR data, the process loops back from step 212 to step 210 and the fit comparison is repeated for the next shape from the shape database.

In step 214, the object type for the compared shape from the shape database and the best probability value for the compared shape are temporarily stored for future comparison and/or output. For example, the compared shape from the shape database can be identified by metadata that is included in the database or embedded in the comparison data. Proceeding to step 216, the process either loops back to step 210 or proceeds to step 218, depending on whether a test is met. If the most recently compared shape is the last shape available for comparison, then the process proceeds to step 218. Optionally, if the most recently compared shape is the last shape that the process has time to compare (for example, if a new MIR data is received and/or if another process requires output data from the process 201) then the process proceeds to step 218. In step 218, the object type and the probability value is output. The process can then loop back to step 202 and the process 201 can be repeated.

Otherwise, the process 201 loops from step 216 back to step 210. Again, in step 210, the next comparison shape from a shape database is loaded. According to an embodiment, the comparison can proceed from the last tested shape in the shape database. In this way, if the step 218 to 202 loop occurs more rapidly than all objects in the shape database can be compared, the process eventually works its way through the entire shape database. According to an embodiment, the shape database can include multiple copies of the same object at different orientations, distances, and positions within the region. This can be useful to reduce processing associated with stepping the MIR shape across the shape database shape and/or changing magnification.

The object type can include determination of a number of persons 112 in the region 110. For example, the shape database can include outlines, cardiac and/or respiration spectra, density, and movement characteristics for plural numbers of persons. According to embodiments, the shape library can include shapes not corresponding to persons. This can aid in identification of circumstances where no person 212 is in the region 210. Optionally, process 201 can be performed using plural video frames such as averaged video frames or a series of video frames. Optionally, steps 212, 214, and 216 can be replaced by a single decision step that compares the probability to a predetermined value and proceeds to step 218 if the probability meets the predetermined value. This can be useful, for example, in embodiments where simple presence or absence of a person 212 in the region 210 is sufficient information.

According to an embodiment, the signal analysis process 201 of FIG. 2 can be performed using conventional software running on a general-purpose microprocessor. Optionally, the process 201 can use various combinations of hardware, firmware, and software; and can include the use of a digital signal processor.

Figure 3:
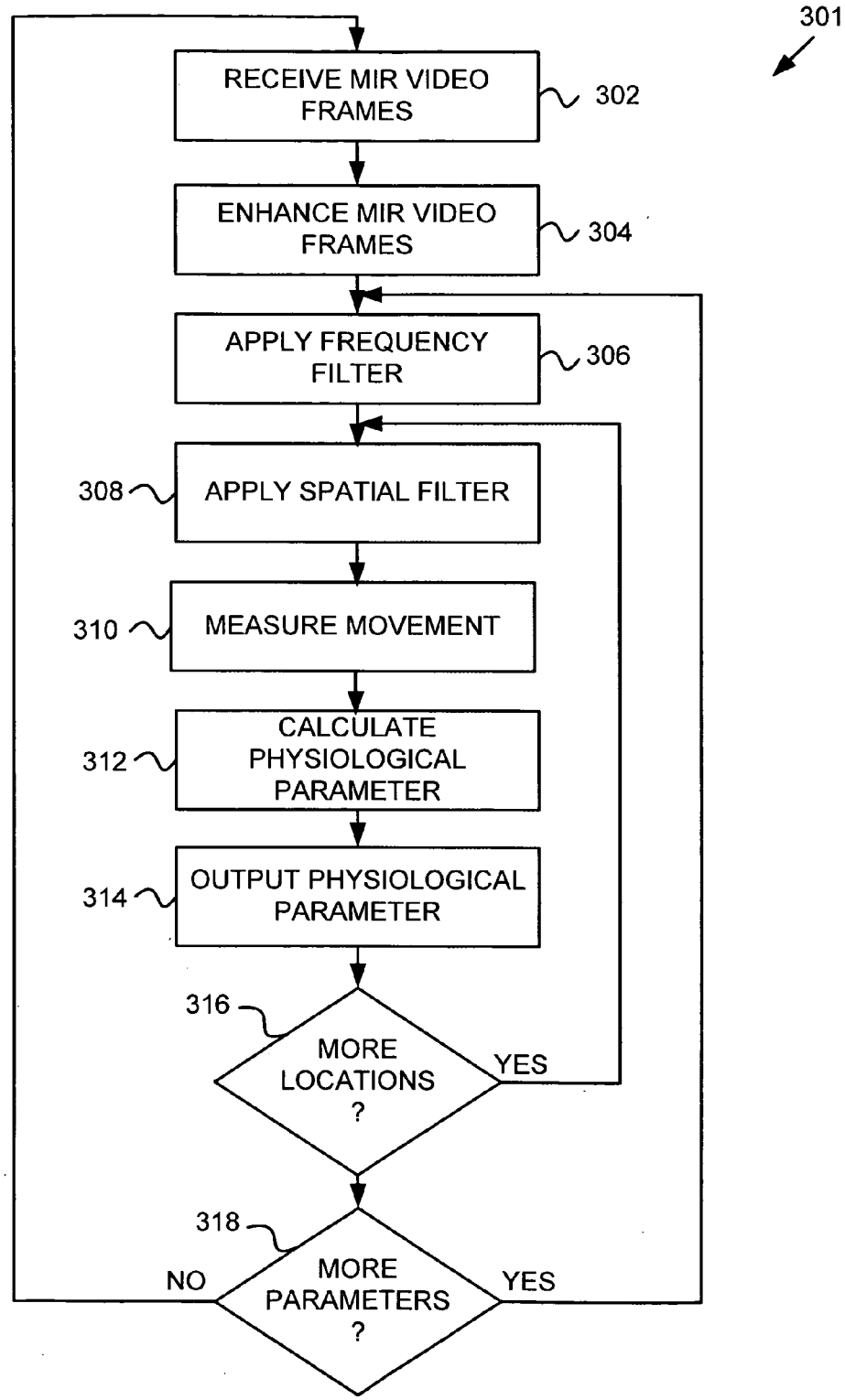
FIG. 3 is a flow chart showing an illustrative process for determining a physiological parameter of a person in a region with the MIR of FIG. 1, according to an embodiment.

FIG. 3 is a flow chart showing an illustrative process 301 for determining one or more particular physiological parameters of a person 112 in the region 110 with the signal analyzer 124 of the MIR 101, according to an embodiment. Optionally, the process 301 of FIG. 3 can be performed conditional to the results of another process such as the process 201 of FIG. 2. For example, if the process 201 determines that no person 112 is in the region 110, then it can be preferable to continue to repeat process 201 rather than execute process 301 in an attempt to extract one or more particular physiological parameters from a person that is not present.

Beginning with step 302, a series of MIR time series data is received. While the received time series data need not be purely sequential, the process 301 generally needs the time series data received in step 302 to have a temporal capture relationship appropriate for extracting time-based information. According to an embodiment, the MIR time series data can have a frame rate between about 16 frames per second and about 120 frames per second. Higher capture rate systems can benefit from depopulating frames, such as by dropping every other frame, to reduce data processing capacity requirements.

Proceeding to step 304, the MIR video frames can be enhanced in a manner akin to that described in conjunction with step 204 of FIG. 2. Optionally, step 304 can include averaging and/or smoothing across multiple MIR time series data. Proceeding to optional step 306, a frequency filter can be applied. The frequency filter can operate by comparing changes between MIR time series data to a reference frequency band for extracting a desired physical parameter. For example, if a desired physiological parameter is a heart rate, then it can be useful to apply a pass band for periodic movements having a frequency between about 20 cycles per minute and about 200 cycles per minute, since periodic motion beyond those limits is unlikely to be related to a human heart rate. Alternatively, step 304 can include a high pass filter that removes periodic motion below a predetermined limit, but retains higher frequency information that can be useful for determining atypical physiological parameters.

Proceeding to optional step 308, a spatial filter can be applied. The spatial filter may, for example, include a pass band filter configured to remove information corresponding to areas of contrast having insufficient physical extent to be large enough to be an object of interest, and remove information corresponding to areas too large to be an object of interest. The spatial filter may, for example, identify portions of the region 110 having sufficient physical extent to correspond to the heart, diaphragm, or chest of a person 112, and remove signal features corresponding to smaller or larger objects. The step of applying the spatial filter 308 can further include removing background features from the MIR data. For example, a wall lying between an antenna 104, 114 (114b) and the region 110 can cast a shadow such as a line in every instance of MIR data. Removal of such constant features can reduce subsequent processing requirements.

Proceeding to step 310, movement such as periodic movement in the MIR time series data is measured. For example, when a periodic motion is to be measured, a time-to-frequency domain transform can be performed on selected signal elements. For example, when a non-periodic motion such as translation or rotation is to be measured, a rate of movement of selected signal elements can be determined. Optionally, periodic and/or non-periodic motion can be measured in space vs. time. Arrhythmic movement features can be measured as spread in frequency domain bright points or can be determined as motion vs. time. Optionally, subsets of the selected signal elements can be analyzed for arrhythmic features. Optionally, plural subsets of selected signal elements can be cross-correlated for periodic and/or arrhythmic features. Optionally, one or more motion phase relationships between plural subsets of selected signal features, between a subset of a selected signal feature and the signal feature, or between signal features can be determined.

For example, a person with a hiccup can be detected as a non-periodic or arrhythmic motion superimposed over periodic motion of a signal element corresponding to the diaphragm of the person.

Proceeding to step 312, a physiological parameter can be calculated. For example, MIR data can include data having a periodic motion spectrum corresponding to the location characteristic of a human physiological process (e.g. heartbeat and/or breathing). Step 312 can include determining one or more heart rates by comparing movement of the heart surface to the MIR signal rate. The one or more heart rates can further be characterized according to a confidence factor, depending on statistical certainty regarding the determined one or more heart rates. Similarly, step 312 can include determining one or more respiration rates by measuring movement corresponding to the chest or diaphragm of one or more persons.

Proceeding to step 314, the physiological parameter can be output. Proceeding to step 316, if there are more locations to measure, the process 301 can loop back to execute step 308. If there are not more locations to measure, the process can proceed to step 318. In step 318, if there are more physiological parameters to measure, the process 301 can loop back to execute step 306. If there are not more physiological parameters to measure, the process 301 can loop back to step 302, and the process 301 of FIG. 3 can be repeated.

Figure 4:
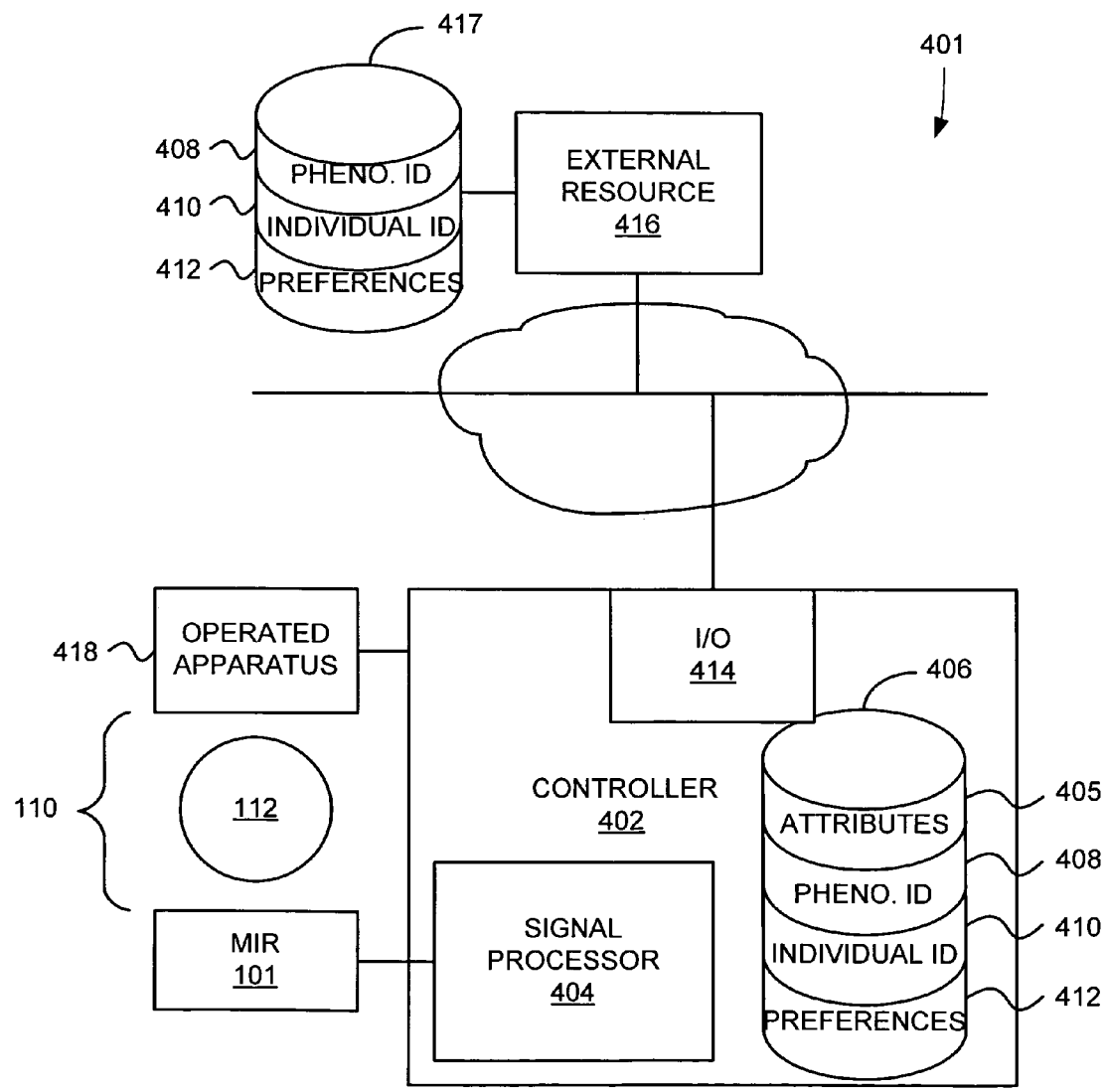
FIG. 4 is a block diagram of a system for providing a probabilistic identification of a person, according to an embodiment.

FIG. 4 is a block diagram of a system 401 for providing a probabilistic identification of a person 112, according to an embodiment. A MIR 101 is configured to capture signals from a region 110. A signal processor 404, which can optionally be integrated into a controller 402 or the MIR 101, is configured to receive the signals from the MIR 101 and extract from the signals information corresponding to at least one attribute corresponding to a person 112. The at least one attribute can include a plurality of attributes corresponding to a human form 112. The plurality of attributes can include at least one physical attribute and/or at least one physiological attribute corresponding to the person 112. A controller 402 is configured to receive the information corresponding to the at least one physical attribute and/or the at least one physiological attribute, and determine a phenotypic identity corresponding to the at least one physical attribute and/or the at least one physiological attribute. An electronic memory or computer storage device 406 is configured to receive and hold the information 408 corresponding to the attribute(s) and the determined phenotypic identity. For example, determining a phenotypic identity can include storing data corresponding to the information in a memory, a look-up table, and/or a database. The controller 402 can include an electronic memory and/or computer storage device 406 configured to hold a tangible computer readable medium carrying a correlation 408 between the phenotypic identity, at least one physical attribute and at least one physiological attribute.

Examples of physical attributes that can be used to determine a phenotypic identity include a size of a person, a shape of a person, density of a person, detectable ornamentation associated with a person, equipment accompanying the person, equipment supporting the person, detectable clothing worn by a person, a heart size, a posture, a head-to-body size ratio, body movements, an in utero fetus, a prosthesis, and/or a personal appliance. Examples of physiological attributes that can be used to determine a phenotypic identity include a heart rate, a heart arrhythmia, a respiration rate, a respiration irregularity, a diaphragm motion, a diaphragm spasm, and/or a detectable health. Examples of equipment accompanying the person can include, for example, equipment that is carried, pushed or pulled by the person. For example, a hand truck, delivery cart, medical therapy apparatus, pharmacy cart, oxygen tank, etc. can tend to indicate a function or a physical requirement of a person, and thereby help identify the person. Examples of equipment supporting the person can include a personal conveyance such as a scooter, bicycle, motorcycle, a wheelchair, or other apparatus that may tend to be physically associated with a given person.

According to embodiments, the phenotypic identity can include data corresponding to one or more of a size of a person, a shape of a person, density of a person, detectable ornamentation associated with a person, equipment accompanying the person, equipment supporting the person, detectable clothing worn by a person, a heart size, a posture, a head-to-body size ratio, body movements, an in utero fetus, a prosthesis, a personal appliance, a heart rate, a heart arrhythmia, a respiration rate, a respiration irregularity, a diaphragm motion, a diaphragm spasm, and/or a detectable health. In other words, the phenotypic identity can include a data corresponding to the detected physical attributes and/or physiological data. For example, a phenotypic identity can include structured data corresponding to "gender: male, carrying: cell phone, glasses, heart rate: 60-65, height: 6'-2"; or "gender: female, carrying: computer, fetus $2^{nd}$ trimester, heart rate: 55-60, height: 5'-6"."

Referring to FIG. 1, the MIR 101 can include a transmitter 108 configured to transmit electromagnetic pulses toward the region 110, a range delay gate 116 configured to delay the pulses, and a receiver 118 synchronized to the range delay gate 116 and configured to receive electromagnetic energy scattered from the pulses and output signals, which can be analog signals. The signals may, for example, include one or more of received radiation samples, raw detector signals, analog signals, digital signals or filtered signals. An analog-to-digital converter 122 can be operatively coupled to the receiver 118 and configured to convert analog signals from the receiver 118 into digital signals.

Referring again to FIG. 4, the signal processor 404 can extract at least one attribute of one or more persons in the region 110, and the controller 402 can save the attribute(s) as data 405 in a memory or storage device 406. The controller 402 can then determining a phenotypic identity using a process including comparing the at least one attribute 405 to one or more phenotypic identities 408 in the memory or storage device 406. For example, the phenotypic identities 408 can include attributes corresponding to one or more persons 112 represented by previously received MIR 101 signals.

Optionally, the controller can be configured to determine the phenotypic identity by performing a joint fit or joint probability approach to matching attributes 405 from two or more individuals to a plurality of phenotypic identities 408. In some circumstances, such a joint fit can give a faster, more certain, or otherwise better answer than a series of one-at-a-time fits.

Alternatively or additionally, the controller 402 can be further configured to, if a best match between the attribute(s) 405 and one or more phenotypic identities 408 fails to meet one or more criteria, store a new phenotypic identity by writing new phenotypic data 408 corresponding to the attribute(s) 405 to the memory or storage device 406.

According to an embodiment, the controller 402 can further include a database server (not shown). Each of the one or more phenotypic identities 408 can be provided as at least one database record including cells carrying data including one or more attribute descriptions, one or more attribute values, one or more attribute ranges, one or more attribute averages, one or more attribute weighted averages, one or more attribute probabilities, and/or one or more functions of previously observed values of an attribute. The controller 402 can be configured to submit a query to the database server (not shown) including one or more arguments corresponding to the at least one attribute extracted from the micro-impulse radar signal. Determining a phenotypic identity can include reading records returned responsive to the database query.

According to embodiments, the phenotypic identities 408 can include data corresponding to frequency domain data and spatial domain data extracted from the signals from the MIR 101. Additionally or alternatively, the phenotypic data 408 can include personal attributes previously entered by the person 112.

The electronic memory or computer storage device 406 can be further configured to hold individual identities 410 corresponding to the phenotypic identities 408. The controller 402 can be further configured to match the phenotypic identity 408 to the individual identity 410 of the person 102. For example, the controller 402 can be configured to match the phenotypic identity 408 to the individual identity 410 of a person 112 by selecting the individual identity having the highest probability of matching the phenotypic identity 408 out of a plurality of individual identities 410. Optionally, the controller can be configured to determine the individual identity by performing a joint fit or joint probability approach to matching phenotypic identities 408 from two or more individuals to a plurality of individual identities 410.

The electronic memory or computer storage device 406 can be further configured to hold one or more preferences 412 corresponding to the phenotypic identity 408. The controller 402 can be further configured to determine one or more preferences 412 corresponding to the phenotypic identity 408 or an individual identity 410 corresponding to the phenotypic identity 408.

The system 401 and/or controller 402 can include a communication interface 414. The controller 402 can be configured to determine the phenotypic identity 408 by transmitting the at least one attribute 405 to a remote resource 416 via the communication interface 414, and receive the phenotypic identity 408 from the remote resource 416 via the communication interface 414. Similarly, the controller 402 can be configured to transmit the phenotypic identity 408 to the remote resource 416 via the communication interface 414, and receive an individual identity 410 corresponding to the phenotypic identity 408 from the remote resource 416 via the communication interface 414. Similarly, the controller 402 can be configured to transmit the phenotypic identity 408 or an individual identity 410 to a remote resource 416 via the communication interface 414, and receive preferences 412 corresponding to the phenotypic identity 408 or individual identity 410 from the remote resource 416 via the communication interface 414.

The remote resource 416 can include one or more electronic memory or storage apparatuses 417 carrying phenotypic identities 408, individual identities 410, and/or preferences 412. The external resource can determine a particular phenotypic identity 408, individual identity 410 and/or preferences 412 as described above responsive to receiving the communication from the controller 402, also described above.

According to an embodiment, the system 401 can include one or more operated apparatuses 418. For example, an operated apparatus 418 can include a media system, a computer system, an environmental control, a vending machine, a multi-user appliance, and/or a motor vehicle. The controller 402 can be configured to determine one or more preferences 412 corresponding to the phenotypic identity 408 or to an individual identity 410 corresponding to the phenotypic identity 408, and operate the one or more operated apparatuses 418 according to the one or more preferences 412. Operating (or maintaining the operation of) the one or more operated apparatus 418 corresponding to the one or more preferences 412 is described more fully in conjunction with FIG. 5 below.

Figure 5:
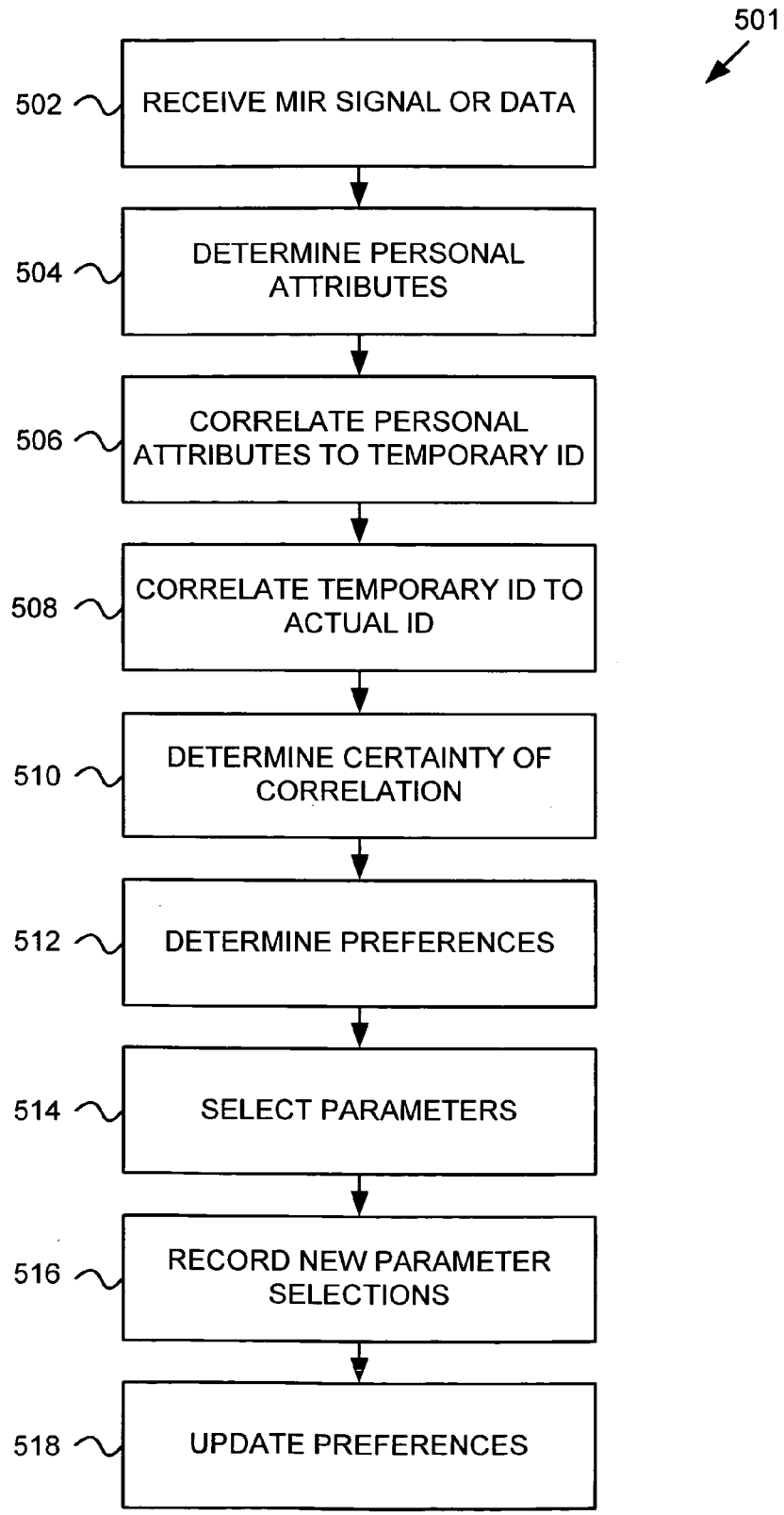
FIG. 5 is a flow chart illustrating a method for correlating a temporary identity determined from a MIR signal to at least one person, according to an embodiment.

FIG. 5 is a flow chart illustrating a method 501 for correlating a temporary identity determined from a micro-impulse radar signal to at least one person, according to an embodiment. Beginning at step 502, MIR data or a MIR signal is received. The micro-impulse radar signal can include a micro-impulse radar image. The micro-impulse radar signal can include micro-impulse radar data. The MIR data or signal can include information associated with at least one person. For example, referring to FIG. 4, the MIR 101 can receive data from a region 110 including a person or persons 112. Referring to FIG. 5, the process 501 proceeds to step 504, where the MIR data or signal is analyzed to determine one or more attributes of the at least one person.

Depending on the application, it may be desirable to select from among a small number (e.g., two) or a relatively large number of persons. For a small relevant population, a small number of attributes can be sufficient to differentiate between the persons. For example, body size alone could be sufficient to determine whether a person is an adult or a child. For a larger relevant population, a larger number of attributes can typically be determined to provide a relatively high probability of an accurate determination and/or differentiation between persons.

According to an embodiment, a limited set of individual identities can be associated with an occupancy record of individuals in or anticipated to be in a region accessed by the MIR. For example, for a household, the limited set of individual identities can correspond to the members of a family living in the household, optionally also including extended family and friends that visit at least on occasion. In another example, the region accessed by the MIR can include all or a portion of a place of business, and the limited set of individual identities can correspond to employees of the business.

According to an embodiment, the one or more attributes of the at least one person can include at least one physical attribute and at least one physiological attribute. For example, a physical attribute can include at least one of body size, body mass, height, body shape, posture, body permittivity, carried articles, and/or detectable body ornamentation. The attributes can include a characteristic movement such as a characteristic voluntary movement or a characteristic involuntary movement. The characteristic movement can include a reactive movement. A physiological attribute can include at least one of heart rate, an intracyclic heartbeat characteristic, breathing rate, a rate or magnitude of inhalation, a rate or magnitude of exhalation, a tremor of all or part of a body, an intracyclic breathing characteristic, or an intercyclic breathing characteristic.

Proceeding to step 506, the one or more attributes is correlated to a temporary identity of one or more persons. The temporary identity is based, at least in part, on the one or more attributes determined in step 504. For example, the temporary identity can correspond to a probabilistic identity. The temporary identity can also correspond to or be referred to as a phenotypic identity.

In some applications, a temporary identity or phenotypic identity can be all that is required. For example, a person checking into a hotel room may select parameters such as room temperature or television volume that establish a set of preferences. According to embodiments, an environment or media controller can later adjust the temperature or television volume to match the preferences without ever having knowledge of the individual identity of the person. Other applications can benefit from knowledge of an individual identity corresponding to the temporary identity. For example, the person checking into the hotel room may have a preference for watching college football games. By correlating the temporary identity to an individual identity, this preference can be conveyed to a media controller, and the media controller can present a range of available televised college football games to the guest or select an appropriate game for presentation.

Step 508 represents an optional step of correlating the temporary identity of the person to an individual identity of the person. In some embodiments, step 508 can include selecting from a limited set of individual identities. Limiting the set of possible individual identities can significantly reduce MIR data collection requirements and/or improve the certainty of correctly selecting the individual identity. Step 508 can include accessing a database or a look-up table. For example, the database or look-up table can include records corresponding to phenotypic identities that include cells providing physical, physiological, and other attributes such as those listed above. A new temporary identity can be compared to determine a best fit from among the records. The best fit record can also include a person's name, one or more cells that act as an index to a person's preferences, and/or other indicators of the individual person. According to embodiments, correlating the temporary identity to an individual identity does not necessarily require determining information that can explicitly identify the person (e.g., provide an actual identity), because in some applications all that is required is the determination of preferences corresponding to the individual identity. Thus, the "individual identity" can include an index number, and the person can remain anonymous to the system; or it can include a conventional identity including the person's name, for example. The correlation of step 508 can occur in real-time, i.e., once the temporary identity is assigned. In other embodiments, step 508 can be performed at a later time, (e.g., after micro-impulse sensing of the individual has ceased, during periodic data review and analysis, etc.).

While step 508 has been described as a local correlation, such correlation can alternatively be performed remotely. For example, with reference to FIG. 4, step 508 can include transmitting the temporary identity to an external resource 414; and receiving, from the external resource 414, information corresponding to a temporary identity and/or the individual identity corresponding to the temporary identity.

Proceeding to optional step 510, the certainty of the correlation can be determined. For example, step 510 can include determining the certainty of correlation to a previously determined temporary identity or phenotypic identity, or it can include determining the certainty of correlation between the temporary identity and an individual identity. For example, the certainty can be expressed as a function of how well the attributes of the temporary identity match stored attributes. If the temporary identity has no detectable ornamentation but the stored temporary or phenotypic identity includes a probability of wearing a detectable wristwatch, such a deviation can be given very low weight. However, if the stored phenotypic identity includes a high probability of a strong wheeze or tremor, but the temporary identity does not possess such an attribute, then the certainty of identification can be relatively low, even if all other attributes match. Conventional statistical analyses can be used to determine the certainty of correlation.

Proceeding to step 512, one or more preferences corresponding to the temporary identity or individual identity are determined. The one or more preferences can related to one or more controlled or operated apparatuses with which the at least one person has a relationship such as a proximity relationship. According to embodiments, the one or more preferences can include one or more of media preferences, computer preferences, environmental preferences, or motor vehicle preferences. As described above, the preferences can be determined locally or by a remote resource. The preferences can be based on observed parameter selections. Alternatively or additionally, the preferences can be selected by the person for use by the process 501 and/or other similar processes that determine or infer an individual identity of a person.

Proceeding to step 514, one or more parameters of the operated apparatus(es) can be selected responsive to the preferences. For example, parameters related to a media system, a computer system, an environmental control, a vending machine, a multi-user appliance, and/or a motor vehicle can be selected responsive to the preferences. For example, selecting one or more parameters of a media system can include selecting a music genre, selecting channel favorites, selecting a media library, selecting an audio volume, selecting an audio balance, selecting an audio equalization, selecting an audio mode, selecting a video mode, selecting a receiver configuration, selecting a media source, selecting a television channel, and/or resetting the media system to a configuration corresponding to a previous instance of the presence of the at least one person. Selecting one or more parameters of a computer system can include selecting an operating system environment, selecting user preferences, selecting one or more application programs, selecting a keyboard configuration, selecting a pointer device configuration, selecting a user profile, selecting a computer system configuration corresponding to a previous instance of the presence of the at least one person, and/or automatically entering a password. Selecting one or more parameters of an environmental control can include selecting a lighting configuration, selecting a thermostat setting, selecting a window treatment configuration, selecting a room or compartment access configuration, or selecting a ventilation configuration. Selecting one or more parameters of a vending machine can include highlighting a typical selection made by a person, suggesting an alternative selection that may appeal to the user, enforcing a controlled substance vending policy, etc. A multi-user appliance can, for example, include a food or drink processor, a massager, a bathtub, a jetted tub, a shower, a kitchen appliance, an elevator, or other apparatus that a given person may typically select a given setting or operation option from a range of settings or options. Selecting one or more parameters of a multi-user appliance may, for example, include selecting a food or drink processor setting; selecting a massage style, location, speed, or intensity; selecting a water temperature, water flow rate, or water jet combination; selecting a kitchen appliance operation mode or interface; or highlighting or selecting a destination floor in an elevator. Selecting one or more parameters of a motor vehicle can include selecting a vehicle access parameter (such as by unlocking a door), selecting a seating position, selecting a throttle gain, selecting a steering response, and/or enabling an ignition.

The method 501 can further include modifying preferences according to observed selections of parameters. Accordingly, optional step 516 includes recording parameters corresponding to the operated apparatus such as a media system, a computer system, an environmental control, a vending machine, a multi-user appliance, or a motor vehicle selected by a person corresponding to the temporary identity or corresponding to an individual identity corresponding to (e.g., correlated to) the temporary identity. The recorded media system, computer system, or environmental system parameters selected by the person can then be recorded as preferences or used to update the preferences of the person, as indicated by step 518. For applications where a longstanding temporary or phenotypic identity or an individual identity is determined, it can be preferable not to update the person's preferences unless the system is relatively certain about the identity of the person. Accordingly, updating preferences can be made (e.g. restricted to instances) when the individual identity is correlated to the temporary identity, or a previously established temporary identity or phenotypic identity is correlated to the temporary identity with a sufficient certainty. Thus, the preferences corresponding to the individual identity can be updated responsive to the recorded media system, computer system, environmental control, or motor vehicle parameters selected by the person.

Optionally, the method 501 can include generating an occupancy record for the person (not shown). For example, an occupancy record can act as a record of presence of the person. Optionally, the occupancy record can be used to determine a limited number of phenotypic identities and/or individual identities to which detected attributes are compared. Similarly, the occupancy record can be used to track behavior of persons. The occupancy record can include a position of the person, a speed of the person, a velocity of the person, a direction of motion of the person, an orientation of the person, a time associated with presence of the person, a time of arrival of the person to a region, and/or a time of departure of the person from the region, for example. The generated occupancy record can optionally be sent to a third party or external database. The occupancy record can additionally or alternatively be combined with another occupancy record associated with the person.

To recapitulate, the method 501 can include receiving a micro-impulse radar signal including information associated with at least one person; performing analysis of the micro-impulse radar signal to determine, from the signal, a plurality of attributes of the at least one person, for example, including at least one physical attribute and at least one physiological attribute; determining a temporary identity of the at least one person based at least in part on the plurality of attributes; comparing the temporary identity to corresponding attributes of a limited number of individual persons; selecting an individual identity or index to an individual identity having a highest probability of being a correct match; determining one or more preferences of a person corresponding to the individual identity or index to the individual identity; and adjusting or maintaining a media parameter, computer system parameter, environmental control parameter, or motor vehicle parameter according to the one or more preferences.

Figure 6:
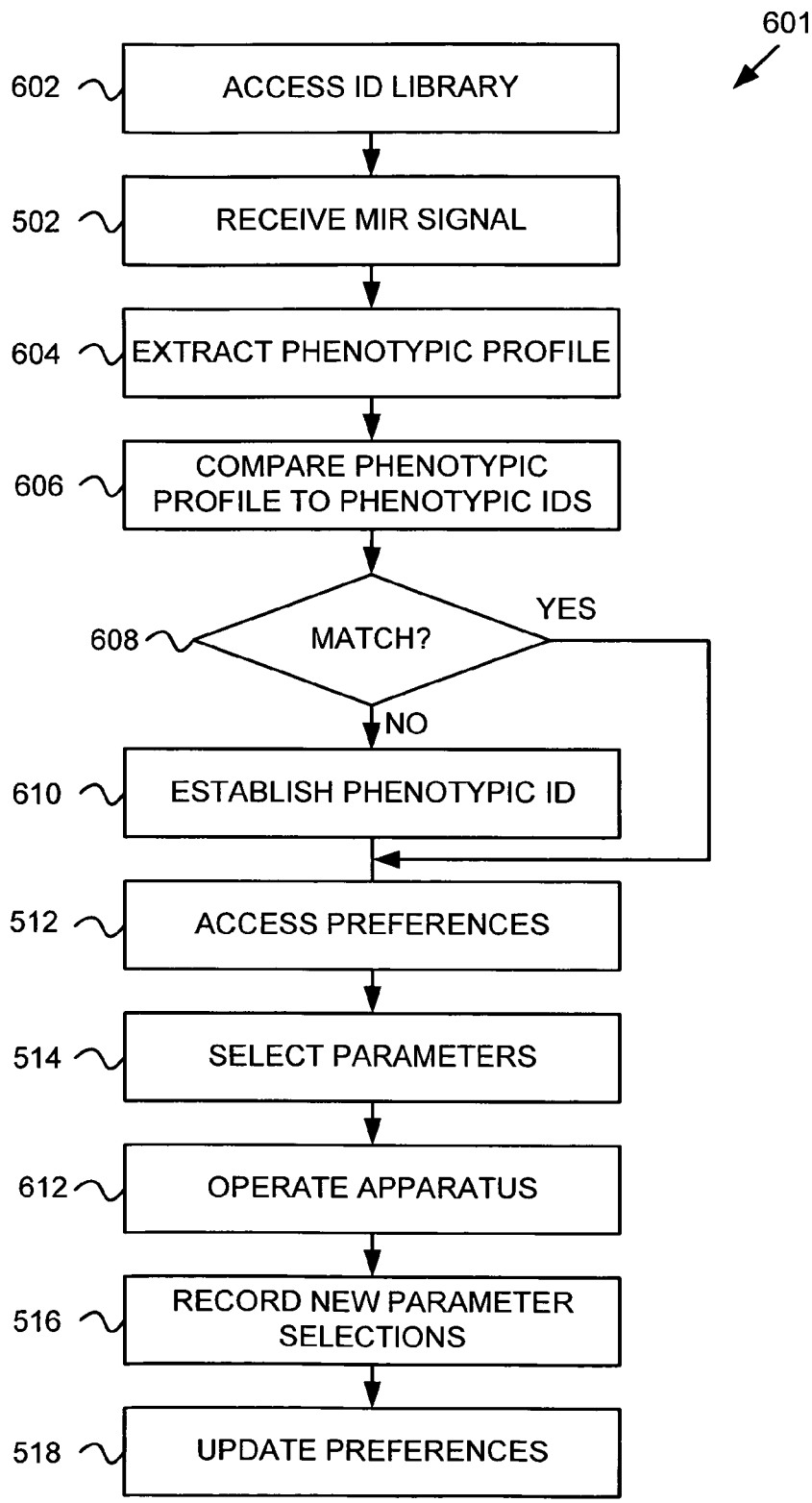
FIG. 6 is a flow chart illustrating a method for identifying an individual from a group of individuals, according to an embodiment.

FIG. 6 is a flow chart illustrating a method 601 for identifying an individual from a group of individuals, according to an embodiment. Beginning at step 602, an identification library including a plurality of individual identities and phenotypic identities is accessed. Step 602 can include accessing a database or a look-up table. The identification library can reside on local memory or storage, or can be provided by a remote resource. Optionally, accessing an identification library can include establishing an identification library.

In some embodiments, the identification library can include a limited set of individual identities. For example, the database or look-up table can include records corresponding to phenotypic identities that include cells providing physical, physiological, and other attributes such as those listed above. A new temporary identity can be compared to determine a best fit from among the records. The best fit record can also include a person's name, one or more cells that act as an index to a person's preferences, and/or other indicators of the individual person. According to embodiments, correlating the temporary identity to an individual identity does not necessarily require determining information that can explicitly identify the person, because in some applications all that is required is the determination of preferences corresponding to the individual identity. Thus, the "individual identity" can include an index number, and the person can remain anonymous to the system; or it can include a conventional identity including the person's name, for example.

According to an embodiment, the one or more attributes making up a phenotypic identity can include at least one physical attribute and at least one physiological attribute. For example, a physical attribute can include at least one of body size, body mass, height, body shape, typical posture, body permittivity, typical carried articles, and/or typical body ornamentation. The attributes can include a characteristic movement such as a characteristic voluntary movement or a characteristic involuntary movement. The characteristic movement can include a reactive movement. A physiological attribute can include typical values for at least one of heart rate, an intracyclic heartbeat characteristic, breathing rate, a rate or magnitude of inhalation, a rate or magnitude of exhalation, a tremor of all or part of a body, an intracyclic breathing characteristic, or an intercyclic breathing characteristic.

The plurality of individual identities and corresponding phenotypic identities can correspond to a small number (e.g., two) or a relatively large number of persons. For a small plurality of individuals, a small number of attributes can make up a phenotypic identity and can be sufficient to differentiate between the persons. For example, in a single parent household, body size alone could be sufficient to determine whether a person is an adult or a child member of the household. For a larger plurality of individual identities and corresponding phenotypic identities, a larger number of attributes can make up a phenotypic identity to provide differentiation between persons.

Proceeding to step 502, at least one MIR signal including information associated with at least one human form is received. Next, in step 604, analysis is performed on the MIR signal to extract a phenotypic profile corresponding to the at least one human form. Proceeding to step 606, the phenotypic profile extracted in step 604 is compared to the plurality of phenotypic identities from the identification library to determine an associated individual identity. As indicated above, the plurality of individual identities in the identification library can correspond to assigned individual characteristics not correlated to actual known identities of individuals. For example, the plurality of individual identities can correspond to individual aliases representative of individual persons. Alternatively, the plurality of individual identities can correspond to actual known identities of individuals.

Optionally, the process 501 can include flagging an individual identity as "in-use" during a time period in which the phenotypic identity is associated with the individual identity. Step 606 can thus include excluding individual identities having "in use" flags. After analysis on a subsequent MIR signal in step 604 determines that the phenotypic profile can no longer be extracted the "in use" flag can be removed from the individual identity.

Optionally, step 606 can include performing a joint fit of two or more phenotypic profiles to a plurality of phenotypic identities. Performing a joint fit or joint probability fit can be advantageous in some applications.

Proceeding to step 608, a determination is made about whether or not a match can be made between the extracted phenotypic profile and a phenotypic identity in the identification library. If it is determined that the extracted phenotypic profile does not correspond to a phenotypic identity in the identification library, then the process 601 proceeds to step 610, where a new phenotypic identity corresponding to the phenotypic profile is established. If it is determined, in step 608, that a match was made, an individual identity can optionally be determined. In any event, in step 512, after a positive determination in step 608 or after step 610, a preference table corresponding to an individual identity and/or an individual phenotypic identity can be accessed. One or more preferences corresponding to an operated device can be read from the preference table. Proceeding to step 514, one or more parameters of a media system, computer system, or an environment corresponding to one or more preferences from the preference table is selected. Next, in step 612, at least one apparatus is operated according to the one or more environmental, media system, or computer system parameters.

For example, if step 612 includes operating a media system, selecting one or more parameters in step 514 can include selecting a music genre, selecting channel favorites, selecting a media library, selecting an audio volume, selecting an audio balance, selecting an audio equalization, selecting an audio mode, selecting a video mode, selecting a receiver configuration, selecting a media source, selecting a television channel, and/or resetting the media system to a configuration corresponding to a previous instance of the presence of the at least one person.

In another example, if step 612 includes operating a computer system, selecting one or more parameters in step 514 can include selecting an operating system environment, selecting user preferences, selecting one or more application programs, selecting a keyboard configuration, selecting a pointer device configuration, selecting a user profile, selecting a computer system configuration corresponding to a previous instance of the presence of the at least one person, and/or automatically selecting a password.

In another example, if step 612 includes operating an environmental control, selecting one or more parameters in step 514 can include selecting a lighting configuration, selecting a thermostat setting, selecting a window treatment configuration, selecting a room or compartment access configuration, selecting a ventilation configuration, selecting a seating position, selecting a throttle gain, selecting a steering response, and/or selecting a parameter for enabling an ignition.

Proceeding to step 516, parameters corresponding to a media system, a computer system, or an environment selected by a person corresponding to the individual identity can be recorded, and in step 518, the parameters can be used to update the preference table.

Referring again to FIG. 4, portions of the methods represented by the flow charts of FIGS. 5 and 6 can be performed by the external resource 416. Accordingly, a phenotypic identity 408, and individual identity 410, and/or preferences 412 can be determined responsive to receiving data corresponding respectively to attributes 405, a phenotypic identity 408, or an individual identity 410 from a local resource. Such determination can be performed substantially as described above with respect to FIG. 4, FIG. 5, and/or FIG. 6.

The methods corresponding to FIGS. 5 and/or 6; and/or the functions described with respect to FIG. 4 can be embodied as computer readable instructions carried by non-transient computer readable media. Thus, the methods can cause one or more computers to perform the steps.

While particular aspects of the present subject matter described herein have been shown and described, it will be apparent that, based upon the teachings herein, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims. It will be understood that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). If a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

With respect to the appended claims, those skilled in the art will appreciate that recited operations therein may generally be performed in any order. Examples of such alternate orderings may include overlapping, interleaved, interrupted, reordered, incremental, preparatory, supplemental, simultaneous, reverse, or other variant orderings, unless context dictates otherwise. With respect to context, even terms like "responsive to," "related to," or other past-tense adjectives are generally not intended to exclude such variants, unless context dictates otherwise.

While various aspects and embodiments have been disclosed herein, other aspects and embodiments are contemplated. The various aspects and embodiments disclosed herein are for purposes of illustration and are not intended to be limiting, with the true scope and spirit being indicated by the following claims.

What is claimed is:

1. A method for correlating a temporary identity to at least one person, comprising:
   receiving a micro-impulse radar signal including information associated with at least one person;
   performing analysis of the micro-impulse radar signal to determine, from the signal, one or more attributes of the at least one person;
   correlating a temporary identity to an individual identity of the at least one person based at least in part on the one or more attributes by performing a joint probability to match the one or more attributes to the individual identity;
   determining one or more preferences corresponding to the temporary identity or to the individual identity;
   selecting one or more parameters of an operated apparatus, the one or more parameters corresponding to the one or more preferences;
   wherein:
   the temporary identity is provided as at least one database record including one or more cells including at least one of one or more attribute descriptions, one or more attribute values, one or more attribute ranges, one or more attribute averages, one or more attribute weighted averages, one or more attribute probabilities, or one or more functions of previously observed values of an attribute; and
   the individual identity is selected from a limited set of individual identities associated with an occupancy record of individuals in or anticipated to be in a region accessed by the micro-impulse radar and includes at least one person's name.

2. The method for correlating a temporary identity to at least one person of claim 1, wherein the at least one attribute of the at least one person includes a plurality of attributes of the at least one person, including at least one physical attribute and at least one physiological attribute.

3. The method for correlating a temporary identity to at least one person of claim 1, wherein the temporary identity corresponds to a phenotypic identity.

4. The method for correlating a temporary identity to at least one person of claim 1, wherein the micro-impulse radar signal includes a micro-impulse radar image.

5. The method for correlating a temporary identity to at least one person of claim 1, wherein the micro-impulse radar signal includes micro-impulse radar data.

6. The method for correlating a temporary identity to at least one person of claim 1, wherein the one or more attributes includes at least one of body size, body mass, height, body shape, posture, body permittivity, carried articles, or detectable body ornamentation.

7. The method for correlating a temporary identity to at least one person of claim 1, wherein the one or more attributes includes a characteristic movement.

8. The method for correlating a temporary identity to at least one person of claim 1, wherein the one or more attributes includes at least one of heart rate, an intracyclic heartbeat characteristic, breathing rate, a rate or magnitude of inhalation, a rate or magnitude of exhalation, a tremor of all or part of a body, an intracyclic breathing characteristic, or an intercyclic breathing characteristic.

9. The method for correlating a temporary identity to at least one person of claim 1, wherein correlating the temporary identity to the individual identity of the at least one person includes at least one of accessing a database or a look-up table.

10. The method for correlating a temporary identity to at least one person of claim 1, further comprising:
determining a statistical certainty of the determined individual identity.

11. The method for correlating a temporary identity to at least one person of claim 1, wherein the operated apparatus includes one or more of a media system, a computer system, an environmental control, a vending machine, a multi-user appliance, or a motor vehicle.

12. The method for correlating a temporary identity to at least one person of claim 1, wherein the operated apparatus includes a media system; and
wherein selecting one or more parameters of the media system includes one or more of selecting a music genre, selecting channel favorites, selecting a media library, selecting an audio volume, selecting an audio balance, selecting an audio equalization, selecting an audio mode, selecting a video mode, selecting a receiver configuration, selecting a media source, selecting a television channel, or resetting the media system to a configuration corresponding to a previous instance of the presence of the at least one person.

13. The method for correlating a temporary identity to at least one person of claim 1, wherein the operated apparatus includes a computer system; and
wherein selecting one or more parameters of the computer system includes one or more of selecting an operating system environment, selecting user preferences, selecting one or more application programs, selecting a keyboard configuration, selecting a pointer device configuration, selecting a user profile, selecting a computer system configuration corresponding to a previous instance of the presence of the at least one person, or automatically entering a password.

14. The method for correlating a temporary identity to at least one person of claim 1, wherein the operated apparatus includes an environmental control; and
wherein selecting one or more parameters of the environmental control includes one or more of selecting a lighting configuration, selecting a thermostat setting, selecting a window treatment configuration, selecting a room or compartment access configuration, or selecting a ventilation configuration.

15. The method for correlating a temporary identity to at least one person of claim 1, wherein the operated apparatus includes a motor vehicle; and
wherein selecting one or more parameters of the motor vehicle includes one or more of selecting a vehicle access configuration, selecting a seating position, selecting a throttle gain, selecting a steering response, or enabling an ignition.

16. The method for correlating a temporary identity to at least one person of claim 1, further comprising:
recording parameters corresponding to the operated apparatus selected by the at least one person corresponding to the temporary identity or the individual identity corresponding to the temporary identity; and
saving the recorded parameters as preferences or combining the recorded parameters with preferences corresponding to the temporary identity or the individual identity corresponding to the temporary identity of the at least one person.

17. The method for correlating a temporary identity to at least one person of claim 1, further comprising:
transmitting the temporary identity to an external resource; and
receiving, from the external resource, one or more at least one preference corresponding to the temporary identity or the individual identity corresponding to the temporary identity.

18. The method for correlating a temporary identity to at least one person of claim 1, wherein correlating the temporary identity to one or more of the at least one person based at least in part on the one or more attributes comprises:
transmitting the one or more attributes to an external resource; and
receiving, from the external resource, the temporary identity.

19. The method for correlating a temporary identity to at least one person of claim 1, further comprising:
comparing the temporary identity to corresponding attributes of a limited number of individual persons;
selecting the individual identity or index to the individual identity having a highest probability of being a correct match;
determining one or more preferences of a person corresponding to the individual identity or index to the individual identity; and
adjusting or maintaining a media parameter, computer parameter, environmental parameter, or motor vehicle parameter according to the one or more preferences.

20. The method for correlating a temporary identity to at least one person of claim 1, further comprising:
generating an occupancy record for the person, the occupancy record including at least one of a position of the person, a speed of the person, a velocity of the person, a direction of motion of the person, an orientation of the person, a time associated with presence of the person, a time of arrival of the person to a region, and a time of departure of the person from the region.

21. The method for correlating a temporary identity to at least one person of claim 20, further comprising:
sending the occupancy record to a third party or external database.

22. The method for correlating a temporary identity to at least one person of claim 20, further comprising:
combining the occupancy record with another occupancy record associated with the person.

23. A system for providing a probabilistic identification of a person, comprising:
a micro-impulse radar configured to capture signals;
a signal processor configured to receive the signals from the micro-impulse radar and extract from the signals information corresponding to at least one attribute corresponding to a human form;
a database server;
a controller configured to receive the information corresponding to the at least one attribute, and determine a phenotypic identity corresponding to the at least one attribute and further configured to match the phenotypic identity to an individual identity of a person by performing a joint probability of two or more phenotypic identities to a plurality of individual identities;
at least one of an electronic memory or a computer storage device configured to receive and hold the information corresponding to the at least one attribute and the determined phenotypic identity;
one or more operated apparatuses; and
wherein the controller is configured to determine the phenotypic identity by comparing the at least one attribute to one or more phenotypic identities stored in the electronic memory or the computer storage device, and to submit a query to the database server including one or more arguments corresponding to the at least one attribute extracted from the micro-impulse radar signal;

wherein determining a phenotypic identity includes reading records returned responsive to the database query;

wherein each of the one or more phenotypic identities is provided as at least one database record including one or more cells including at least one of one or more attribute descriptions, one or more attribute values, one or more attribute ranges, one or more attribute averages, one or more attribute weighted averages, one or more attribute probabilities, or one or more functions of previously observed values of an attribute;

wherein the individual identity is selected from a limited set of individual identities associated with an occupancy record of individuals in or anticipated to be in a region accessed by the micro-impulse radar and includes at least one person's name;

wherein the controller is further configured to determine one or more preferences corresponding to the phenotypic identity or to the individual identity corresponding to the phenotypic identity and to operate the one or more apparatuses or maintain the operation of the one or more apparatuses according to the one or more preferences.

24. The system for providing a probabilistic identification of a person of claim 23, wherein at least one attribute corresponding to the human form includes a plurality of attributes corresponding to the human form.

25. The system for providing a probabilistic identification of a person of claim 24, wherein the plurality of attributes include at least one physical attribute and at least one physiological attribute.

26. The system for providing a probabilistic identification of a person of claim 23, wherein the at least one attribute includes at least one physical attribute; and wherein the at least one physical attribute includes one or more of a size of a person, a shape of a person, density of a person, detectable ornamentation associated with a person, equipment accompanying the person, equipment supporting the person, detectable clothing worn by a person, a heart size, a posture, a head-to-body size ratio, body movements, an in utero fetus, a prosthesis, or a personal appliance.

27. The system for providing a probabilistic identification of a person of claim 23, wherein the at least one attribute includes at least one physiological attribute; and wherein the at least one physiological attribute includes one or more of a heart rate, a heart arrhythmia, a respiration rate, a respiration irregularity, a diaphragm motion, a diaphragm spasm, or a detectable health.

28. The system for providing a probabilistic identification of a person of claim 23, further comprising assigning the phenotypic identity by storing data corresponding to the information in one or more of a memory, a look-up table, or a database.

29. The system for providing a probabilistic identification of a person of claim 23, wherein the phenotypic identity includes data corresponding to one or more of a size of a person, a shape of a person, density of a person, detectable ornamentation associated with a person, equipment accompanying the person, equipment supporting the person, detectable clothing worn by a person, a heart size, a posture, a head-tobody size ratio, body movements, an in utero fetus, a prosthesis, a personal appliance, a heart rate, a heart arrhythmia, a respiration rate, a respiration irregularity, a diaphragm motion, a diaphragm spasm, or a detectable health.

30. The system for providing a probabilistic identification of a person of claim 23, wherein the controller is further configured to, if a best match between the at least one attribute and the phenotypic identity fails to meet one or more criteria, store a new phenotypic identity by writing new phenotypic data corresponding to the at least one attribute to the memory or storage device.

31. The system for providing a probabilistic identification of a person of claim 23, wherein the one or more phenotypic identities correspond to attributes corresponding to one or more persons represented by previously received micro-impulse radar signals.

32. The system for providing a probabilistic identification of a person of claim 23, wherein each phenotypic identity includes data corresponding to one or more of frequency domain data and spatial domain data extracted from the micro-impulse radar signals.

33. The system for providing a probabilistic identification of a person of claim 23, wherein the electronic memory or computer storage device is further configured to hold the individual identity corresponding to the phenotypic identity.

34. The system for providing a probabilistic identification of a person of claim 23, wherein the electronic memory or computer storage device is further configured to hold one or more preferences corresponding to the phenotypic identity.

35. The system for providing a probabilistic identification of a person of claim 23, wherein the controller is further configured to determine one or more preferences corresponding to the phenotypic identity or the individual identity corresponding to the phenotypic identity.

36. The system for providing a probabilistic identification of a person of claim 23, further comprising:
a communication interface; and
wherein the controller is configured to determine the phenotypic identity by transmitting the at least one attribute to a remote resource via the communication interface, and receive the phenotypic identity from the remote resource via the communication interface.

37. The system for providing a probabilistic identification of a person of claim 23, further comprising:
a communication interface; and
wherein the controller is further configured to transmit the phenotypic identity to a remote resource via the communication interface, and receive the individual identity corresponding to the phenotypic identity from the remote resource via the communication interface.

38. The system for providing a probabilistic identification of a person of claim 23, further comprising:
a communication interface; and
wherein the controller is further configured to transmit the phenotypic identity or the individual identity to a remote resource via the communication interface, and receive preferences corresponding to the phenotypic identity or individual identity from the remote resource via the communication interface.

39. The system for providing a probabilistic identification of a person of claim 23, wherein the operated apparatus includes a media system, a computer system, an environmental control, a vending machine, a multi-user appliance, or a motor vehicle.

40. The system for providing a probabilistic identification of a person of claim 23, wherein the operated apparatus includes a media system; and
wherein determining one or more parameters of the media system includes one or more of determining a music genre, determining channel favorites, determining a media library, determining an audio volume, determining an audio balance, determining an audio equalization, determining an audio mode, determining a video mode, determining a receiver configuration, determining a media source, determining a television channel, or resetting the media system to a configuration corresponding to a previous instance of the presence of the at least one person.

41. The system for providing a probabilistic identification of a person of claim 23, wherein the operated apparatus includes a computer system; and wherein determining one or more parameters of the computer system includes one or more of determining an operating system environment, determining user preferences, determining one or more application programs for selection, determining a keyboard configuration, determining a pointer device configuration, determining a user profile, determining a computer system configuration corresponding to a previous instance of the presence of the at least one person, or determining a password.

42. The system for providing a probabilistic identification of a person of claim 23, wherein the operated apparatus includes an environmental control; and wherein determining one or more parameters of the environmental control includes one or more of determining a lighting configuration, determining a thermostat setting, determining a window treatment configuration, determining a room or compartment access configuration, or determining a ventilation configuration.

43. The system for providing a probabilistic identification of a person of claim 23, wherein the operated apparatus includes a motor vehicle; and wherein determining one or more parameters of the motor vehicle includes one or more of determining a vehicle access configuration, determining a seating position, determining a throttle gain, determining a steering response, or enabling an ignition.

\* \* \* \* \*